United States Patent [19]

Petroff et al.

[11] Patent Number: 5,145,978
[45] Date of Patent: Sep. 8, 1992

[54] POSTEMERGENT HERBICIDE COMPOSITIONS CONTAINING SILICONE GLYCOL ADJUVANTS

[75] Inventors: Lenin J. Petroff, Bay County; David J. Romenesko; Robert A. Ekeland, both of Midland County, all of Mich.

[73] Assignee: Dow Corning Corporation, Midland, Mich.

[21] Appl. No.: 653,373

[22] Filed: Feb. 11, 1991

Related U.S. Application Data

[60] Division of Ser. No. 508,029, Apr. 11, 1990, Pat. No. 5,017,216, which is a continuation-in-part of Ser. No. 274,067, Nov. 21, 1988, abandoned, which is a continuation-in-part of Ser. No. 232,737, Aug. 15, 1988, abandoned.

[51] Int. Cl.$^5$ .............................. C07F 7/02; C07F 7/04
[52] U.S. Cl. .................................... 556/437; 556/445; 556/456; 71/91; 71/116; 71/108; 71/124; 71/DIG. 1
[58] Field of Search .................. 556/445, 456, 437; 71/91, 116, 108, 124, DIG. 1

[56] References Cited

U.S. PATENT DOCUMENTS 3,299,112  1/1967  Bailey ................................ 556/445
4,656,162  4/1987  Itoh et al. ............................ 514/63

FOREIGN PATENT DOCUMENTS 59-017551  1/1984  Japan.
1255249  12/1971  United Kingdom.

OTHER PUBLICATIONS

Balneaves, John M. "Proc. 39th N.Z. Weed and Pest Control Conf.", pp. 98-101 (1985).
Union Carbide Corporation, "Silicones for the Agricultural Industry", 23 pages (1984).
Union Carbide Corporation, "Surface Active Copolymers", 17 pages, 1983.
Union Carbide Corporation, "SILWET Surfactants for Use in Agriculture", 1983.

*Primary Examiner*—Richard L. Raymond
*Assistant Examiner*—B. Bembenick
*Attorney, Agent, or Firm*—Alexander Weitz

[57] ABSTRACT

There is disclosed a herbicide composition in which a postemergent herbicide is activated by the inclusion of a silicone glycol adjuvant consisting essentially of (i) a silicone glycol having an average of 4 or 5 ethylene oxide units in its glycol chain and (ii) a silicone glycol dispersant compound for component (i). The composition provides enhanced phytotoxicity in the control of weeds, particularly velvetleaf plants, and shows an improved degree of rainfastness relative to prior art compositions.

5 Claims, No Drawings

POSTEMERGENT HERBICIDE COMPOSITIONS CONTAINING SILICONE GLYCOL ADJUVANTS

This is a divisional of copending application Ser. No. 07/508,029 filed on Apr. 11, 1990 (now U.S. Pat. No. 5,017,216).

Which is a continuation-in-part of co-pending application Ser. No. 07/274,067 filed on Nov. 21, 1988 now abandoned, which is a continuation-in-part of Ser. No. 07/232,737, filed Aug. 15, 1988, now abandoned.

This invention relates to postemergent herbicide formulations. More particularly, the present disclosure relates to a composition of a postemergent herbicide which is activated by the inclusion of a particular silicone glycol adjuvant consisting essentially of (i) a silicone glycol having an average of 4 or 5 ethylene oxide units in its glycol chain and (ii) a silicone glycol dispersant compound for (i).

BACKGROUND OF THE INVENTION

It is well recognized in the art that the full potency of a given organic herbicide is not generally attained without the inclusion of various adjuvants, an adjuvant being broadly defined as any substance which enhances the effectiveness of the herbicide. Thus, for example, through proper formulation with an activity-increasing adjuvant, the damage inflicted upon a particular plant species by an herbicide can be amplified many fold. Such an activity-increasing adjuvant does not generally have biological activity on its own but only brings out the activity of the herbicide.

An example of the aforementioned activity-increasing adjuvants is the class of surfactants known as silicone glycols. These liquids have been shown to enhance the efficacy of various herbicides. L. L. Jansen (Weed Science, v. 21, pages 130-135, March, 1973) examined the effect of adding various silicone glycol adjuvants to different herbicides and found that these adjuvants were superior to a standard organic surfactant in eight plant species. In this study, cationic amino silicone surfactants were also evaluated, but found to be less effective than the organic material. In any event, no specific structures of the silicone compounds were provided in this paper.

Great Britain Patent Number 1,255,249 to Dow Corning Corporation again discloses herbicide compositions employing silicone glycol copolymers. Here, general utility of a large number of adjuvants is professed, as exemplified by two generic silicone glycol formulas which embrace structures having both diorganosiloxane units and alkyl-glycol siloxane units. There is also provided a wide-ranging list of suitable herbicides. This reference, however, provides little direction to those skilled in the art as to which particular silicone glycol structures are to be advantageously combined with specific herbicides, save for two examples employing a triazine herbicide in conjunction with an adjuvant having 1.8 siloxy units and bearing a glycol chain having 12 ethylene oxide units.

In addition to the herbicidal enhancement provided by the activity-increasing adjuvants discussed above, it is often important that herbicide formulations retain a significant degree of activity when plants treated therewith are exposed to rain shortly after application, this being a definition of the degree of "rainfastness." This is particularly critical in the case of water-soluble postemergent herbicides, such as acifluorfen-sodium, which are easily washed away by rainfall occurring within about six hours of application. Typically, this problem is currently addressed by inclusion of another class or adjuvants in the herbicide formulation, namely "sticking agents." The main function of these materials, as the appellation implies, is to impart an increased measure of adhesion of the herbicide composition to plant foliage and thus prevent premature washing away should precipitation occur after the plants are sprayed. The sticking agents are usually polymeric compounds which are generally water-insoluble and tacky in nature.

Neither of the above references addresses the issue of rainfastness nor do these references suggest to those of ordinary skill in the art how particular silicone glycol compounds may be employed to provide both enhanced herbicidal activity to particular herbicides as well as increased rainfastness in the very same formulation, without resorting to the use of additional sticking agents.

SUMMARY OF THE INVENTION

It has now been found that the rainfastness of a postemergent herbicide can be synergistically increased by the inclusion of a combination of a silicone glycol, and a dispersant for the silicone glycol, in the herbicide composition. Quite surprisingly, the improvement in rainfastness resulted only when the silicone glycol had an average of four or five ethylene oxide units in its glycol chain. Contrarily, neither the silicone glycols of the present invention, nor the dispersants therefore, provided rainfastness when used as the sole adjuvant in conjunction with the herbicide. The present invention therefore relates to a composition consisting essentially of:

(I) a postemergent herbicide; and
(II) from about 0.01 to 50 parts by weight, for each part by weight of said herbicide (I), of a silicone glycol adjuvant consisting essentially of
  (i) from 20 to 95 weight percent of a silicone glycol having the average structure

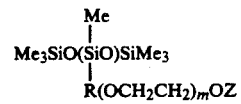

wherein Me denotes a methyl radical, R is a divalent alkylene group having 2 to 6 carbon atoms, Z is selected from the group consisting of hydrogen, an alkyl radical having 1 to 3 carbon atoms and an acyl group having 2 to 4 carbon atoms, and m is 4 or 5, and
  (ii) from 80 to 5 weight percent of a silicone glycol dispersant having the average formula

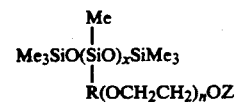

wherein Me, R and Z have their previously defined meanings, n is about 8 to 24 and x is 1 to 5.

The present invention further relates to a method for inhibiting the growth of weeds, particularly velvetleaf plants, comprising contacting at least part of the weed with a herbicidal formulation, the improvement comprising using as said herbicidal formulation a homogeneous aqueous dispersion of the aforementioned composition.

The present invention also relates to the above-mentioned silicone glycol (i) compound which is used in conjunction with said silicone glycol dispersant (ii).

DETAILED DESCRIPTION OF THE INVENTION

The herbicidal composition of the present invention is a homogeneous mixture consisting essentially of (I) a postemergent herbicide, (II) a silicone glycol adjuvant consisting essentially of (i) a silicone glycol having four or five ethylene oxide units in its glycol chain and (ii) a silicone glycol dispersant for silicone glycol (i), which imparts water dispersibility to said composition.

The postemergent herbicide (I) of the present invention is selected from those herbicides well known in the art to be effective when applied after the emergence of a plant. Examples of such postemergent herbicides include, inter alia, 3-isopropyl-1H-2,1,3-benzothiadiazin-4(3H)-one 2,2-dioxide (bentazon) and N-(phosphonomethyl)glycine (glyphosate). The former herbicide is marketed under the trade name BASAGRAN by BASF Wyandotte Corp., Parsippany, NJ and the latter herbicide is sold under the trade name ROUNDUP by Monsanto Agricultural Products Co., St. Louis, Mo.

For the purposes of the present invention, the herbicide may also be selected from the diphenyl ether structures exemplified by the general formula

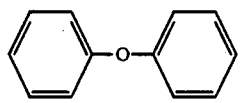

Specific examples of this class of herbicides include such compounds as 2,4-dichlorophenyl 4-nitrophenyl ether (nitrofen); 5-(2-chloro-4-trifluoromethylphenoxy)-2-nitrobenzoic acid (acifluorofen); ethoxycarbonylmethyl 2-[3-(2,6-dichloro-4-trifluoromethyl-phenoxy)-6-nitrophenoxy]-propionate; ethoxymethyl 2-[3-(chloro-4-trifluoromethyl-phenoxy)-6-nitrophenoxy]-propionate; sodium 5-[2-chloro-4-(trifluoromethyl)-phenoxy]-2-nitrobenzoate (acifluorfen-sodium); methyl 5-(2,4-dichlorophenoxy)-2-nitrobenzoate (bifenox); and 2-chloro-1-(3-ethoxy-4-nitrophenoxy)-4-(trifluoromethyl) benzene (oxyfluorfen). For the purposes of the present invention, acifluorfen-sodium is a preferred herbicide.

The silicone glycol (i) of the present invention has the average structure

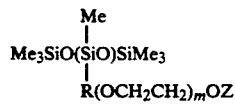

wherein Me hereinafter denotes a methyl radical and R is a divalent alkylene group having 2 to 6 carbon atoms, such as ethylene, trimethylene, tetramethylene or hexamethylene. It is preferred that R is a trimethylene group. In the above formula, Z is selected from the group consisting of hydrogen, an alkyl radical having 1 to 3 carbon atoms and an acyl group having 2 to 4 carbon atoms. Preferably, Z is an acetoxy group. For the purposes of the present invention, it is critical that the value of m is fixed at 4 or 5, preferably 4, ethylene oxide (EO) units.

The silicone glycols described above are well known in the art and may be prepared by coupling the corresponding allyl-terminated glycol to a bis-siloxane structure having a hydrogen attached to the central silicon atom, said structure being

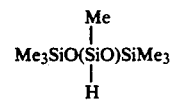

Generally, the coupling is accomplished in the presence of a platinum catalyst. The skilled artisan will recognize that, in such coupling reactions, a fraction of the allyl-terminated glycol is not converted and will remain as an impurity in the final silicone glycol product. Additionally, as a result of inefficient distillation, the allyl-terminated glycol employed may contain a minor proportion of molecules having less than 4, or more than 5, ethylene oxide units. This, in turn, results in silicone glycols having a value of m of less than 4 or greater than 5, respectively. The herbicide compositions may contain such impurities and still be within the scope of the present invention.

The silicone glycol dispersant (ii) of the present invention is similar to the above described silicone glycol (i) and has the average formula

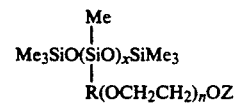

wherein R and Z have their previously defined meanings, but may be assigned independently from component (i). In the above formula, n is about 8 to 24 and x is 1 to 5. It is preferred that x is 1 and n is about 12.

A highly preferred silicone glycol dispersant of the present invention has the average structure

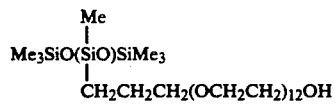

While not wishing to be bound by any particular theoretical explanation for the synergistic effect of components (i) and (ii), it is to be noted that the silicone glycol dispersant (ii) imparts water dispersibility to the combination of the herbicide (I) and silicone glycol (i), since component (i) is itself not readily dispersed in water to form a stable system.

In addition to the aforementioned components, the compositions of the present invention may also contain other herbicide adjuvants commonly employed in the art. Examples of such adjuvants include crop oil concentrate, ORTHO X-77 spreader, drift control agents, such as LO-DRIFT, defoaming agents, such as D-FOAMER, other compatibility agents, such as E-Z MIX, and other adjuvants well known in the herbicide art.

In order to prepare the compositions of the present invention, from about 20 to 95 weight percent of silicone glycol (i) is first thoroughly mixed with from about 80 to 5 weight percent of the silicone glycol dispersant (ii) to form the silicone glycol adjuvant (II). The optimum ratio of these ingredients dependent upon the particular silicone glycol dispersant employed and is readily determined through routine experimentation by the skilled artisan. As intimated above, the amount of silicone glycol dispersant needed to obtain a stable, uniform water dispersion of the components is used to form the compositions of the present invention. By "stable" it is meant herein that the aqueous dispersion does not phase-separate upon prolonged storage at ambient conditions. Generally, the minimum amount of silicone glycol dispersant compatible with this function, and the above noted percentage limits, is so employed.

The above mentioned silicone glycol adjuvant (II) is then preferably blended with herbicide (I) to form a homogeneous dispersion which can then be diluted with water and sprayed onto plants according to the method of the present invention, described infra. Alternatively, the silicone glycol adjuvant (II) may be added directly to a water solution or dispersion of herbicide (I).

In order to be within the scope of the present invention, from about 0.01 to 50 parts by weight of the silicone glycol adjuvant (II) are used for each part by weight of herbicide (I). Preferably, from about 0.2 to 17 parts by weight of the silicone glycol adjuvant (II) are so employed.

Preferred embodiments of the present invention employ a silicone glycol having four ethylene oxide units in its molecule and the highly preferred silicone glycol dispersant, described above, in a weight ratio of about 2:1 to 9:1, respectively. In a particularly preferred embodiment, this ratio is 4:1 and about 5 parts by weight of silicone glycol adjuvant (II) is used for each part by weight of herbicide (I).

In another aspect, the compositions of the present invention consist essentially of from about 0.02 to 2.0 parts by weight of postemergent herbicide (I), from about 0.01 to 50 parts by weight, for each part by weight of said herbicide (I), of the silicone glycol adjuvant (II) and sufficient water to provide 100 parts by weight of the total composition.

The present invention also relates to a method for inhibiting the growth of weeds, particularly the species Abutilon theophrasti, hereinafter referred to by its common name of "velvetleaf." This method comprises contacting at least part of the weed with a homogeneous water dispersion of a herbicidal composition, as hereinabove described. This water dispersion is applied to the foliage of the weed by any of the methods commonly practiced in the art, preferably by spraying. The amount of the dispersion, and the herbicide contained therein, to be applied to the velvetleaf may be varied to a great extent, the optima being determined by such factors as soil conditions, weather conditions and the type of crops or other plants growing alongside the weed. Generally, however, the effective range is about 0.12 to 2 pounds per acre of herbicide formulation.

When the compositions of the present invention are used according to the above described method, there is observed a marked improvement in the rainfastness of the herbicide compositions relative to those containing silicone glycol adjuvants having less than 4 or more than 5 (on average) ethylene oxide units in the glycol chain. Thus, when compared with currently used silicone glycol adjuvants, there is provided a distinct advantage by the instant compositions in that they permit the use of lower herbicide levels to attain a similar degree of injury to a weed when there is a reasonable likelihood of precipitation after broadcasting the herbicide. Such a reduction in herbicide levels generally results in reduced insult to adjacent cash crops and is considered highly desirable.

EXAMPLES

The following examples are presented to further illustrate the compositions of this invention, but are not to be construed as limiting the invention, which is delineated in the appended claims. All parts and percentages in the examples are on a weight basis unless indicated to the contrary.

In a first experimental series (Examples 1-7), the silicone glycols employed had the average structure

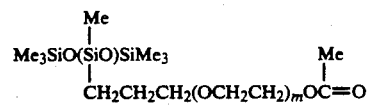

wherein Me hereinafter denotes a methyl radical and m had the value indicated in the table below.

| Silicone Glycol | m (Number of Ethylene Oxide Units) | Purity (By Gas Chromatograph) |
| --- | --- | --- |
| SILICONE GLYCOL A | 1 | 100% |
| SILICONE GLYCOL B | 2 | 95.5% |
| SILICONE GLYCOL C | 3 | 89% |
| SILICONE GLYCOL D | 4 | 82% |
| SILICONE GLYCOL E | 5 | 75% |
| SILICONE GLYCOL F | 6 | 75% |
| SILICONE GLYCOL G | 7 (average) | 75% |

These compounds were prepared by the platinum catalyzed addition of the appropriate allyl-terminated glycol to an organohydrogenpolysiloxane having the structure

Glycols having 1 to 5 ethylene oxide (EO) units were distilled under vacuum to obtain purities in the range of 96%+ (determined by gas-liquid chromatography). These were then coupled to the distilled organohydrogenpolysiloxane to produce SILICONE GLYCOLS A through E. SILICONE GLYCOL F was likewise prepared from a glycol having 6 EO units which was stripped of glycols having less than six ethylene oxide, also under vacuum. SILICONE GLYCOL G was formed from undistilled materials and had an average of 7 EO units in its glycol chain. The impurities in the silicone glycols shown in the above table consisted mainly of the respective beta-isomerized glycols.

A highly preferred dispersant of the present invention having the average structure

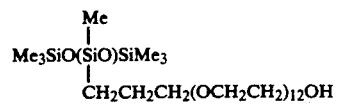

was employed, and will be referred to as DISPERSANT 1 herein.

The herbicide used in the examples was acifluorfen-sodium marketed by BASF Corporation (Research Triangle Park, NC) under the trade name BLAZER.

Additionally, for comparison, a standard organic surfactant, HERBIMAX, was used as an adjuvant with the BLAZER herbicide (Comparative Example 8). HERBIMAX (Loveland Industries, Loveland, CO) is described as a balanced system of oil and surfactants designed to optimize performance of various herbicides in postemergence applications. It contains 17% of a surfactant blend and 83% paraffinic petroleum oil. The following herbicide mixtures were prepared:

EXAMPLES 1-5

Water dispersions of herbicide compositions were prepared by first mixing SILICONE GLYCOL A through SILICONE GLYCOL E with DISPERSANT 1 in a 4:1 ratio. These mixtures (0.94 gm each) were then blended with BLAZER (0.18 gm each) and each blend was diluted with water to provide 250 ml of total dispersion.

EXAMPLES 6-7

Water dispersions similar to those of Examples 1-5 were prepared using SILICONE GLYCOL F and SILICONE GLYCOL G as adjuvants (0.94 gm) together with BLAZER (0.18 gm). No dispersant was employed in these examples and the dispersions were again diluted with water to 250 ml.

EXAMPLE 8

An herbicide formulation containing 0.18 gm BLAZER and 2.5 ml (2.2 gm) of HERBIMAX was prepared by throughly mixing these ingredients and diluting with water, as before.

TEST PROTOCOL

Individually potted velvetleaf plants were grown under standard greenhouse conditions in BACCTO professional potting soil mix. Temperature was controlled at $75 +/- 2°$ F. Irradiation consisted of normal sunlight supplemented by high-pressure sodium vapor lamps to provide an added 1,200 $\mu E/m^2 \cdot s$ at bench level ($\mu E$ = microeinstein), wherein the day/night cycle was set at 18 hours and 6 hours, respectively.

When the plants were 3 to 5 inches tall, they were sprayed with water dispersions of the herbicide compositions so as to broadcast herbicide (i.e., BLAZER) at a rate of 0.03 pounds per acre (0.03 lb/A) along with the adjuvant (i.e., silicone glycol plus dispersant, when used) at a rate of ¾ pint/A. Spraying was accomplished by means of a link-belt sprayer fitted with a TEEJET 8001 E nozzle which delivered the equivalent of 25 gallons/acre of the herbicide dispersion. The BLAZER application rate employed was previously found to induce approximately 50% injury to the velvetleaf after 7 days when an adjuvant, consisting of an 80/20 mix of a crude version of SILICONE GLYCOL D (i.e., prepared from undistilled materials) and DISPERSANT 1, was mixed with BLAZER and broadcast at the above rates. In the spray apparatus employed, the 250 ml samples, described above, provided the prescribed broadcast rates, except for the case of HERBIMAX, which was broadcast at a rate of 1 quart/acre.

In addition, the rainfastness of the herbicide compositions was evaluated by spraying half the plants with water in order to simulate rainfall. This procedure consisted of spraying plants from above (8–10 inches above plant tops) using a TEEJET nozzle which delivered 0.4 gallons of water per minute. This nozzle was also mounted on a chain drive and reciprocally moved over four plants at a time, each such traverse taking about 9–10 seconds. The water spray was started 15 minutes after application of the herbicide compositions and was continued for approximately 7 minutes, at which point the equivalent of one inch of "rain" had fallen on each plant.

Plant injury was visually determined using a double-blind experimental mode wherein four replicates were run for each herbicide composition. Phytotoxicity was ranked from zero, corresponding to no observable effect, to 100%, corresponding to total destruction of the plant. These results were averaged and the values reported using Duncan's multiple range test to distinguish statistical differences at the 95% confidence level. As is common practice in the art, the injury values reported infra include lower case superscript letters which indicate whether any given set of values is statistically identical. Thus, for example, when two injury values have such a superscript in common, this is an indication that these values are not statistically different at the 5% level by Duncan's method.

The above described herbicide dispersions were used to spray velvetleaf plants and the degree of injury, both with and without rain simulation, was observed seven days after spraying with the herbicide dispersions of Examples 1-8. These results, along with the Duncan statistical annotations, are presented in Table 1. As a control, four velvetleaf plants were observed which were not sprayed with any herbicide composition.

TABLE 1

| Herbicide Dispersion | | | DISPERSANT 1 Amount (gm)* | Percent Injury to Plant | |
|---|---|---|---|---|---|
| | | | | No Rain | With Rain |
| | | Silicone | | | |
| | Silicone Glycol | Glycol Amount (gm)* | | | |
| Example 1 | A | 0.752 | 0.188 | $33^{d,e}$ | $10^{i,j}$ |
| Example 2 | B | 0.752 | 0.188 | $50^c$ | $23^{f,g}$ |
| Example 3 | C | 0.752 | 0.188 | $48^c$ | $20^{g,h}$ |
| Example 4 | D | 0.752 | 0.188 | $80^{a,b}$ | $38^d$ |
| Example 5 | E | 0.752 | 0.188 | $75^b$ | $30^e$ |
| Example 6 | F | 0.94 | None | $85^a$ | $20^{g,h}$ |
| Example 7 | G | 0.94 | None | $50^c$ | $20^{g,h}$ |
| | Adjuvant | Adjuvant Amount (gm)* | | | |
| Example 8 | HERBIMAX | 2.2 | None | 15 | 0 |

TABLE 1-continued

| Herbicide Dispersion | DISPERSANT 1 Amount (gm)* | Percent Injury to Plant | |
|---|---|---|---|
| | | No Rain | With Rain |
| (Control - No BLAZER, No adjuvants) | | | |

*In the spray apparatus employed, the 250 ml aqueous dispersions of the examples provided a total silicone glycol adjuvant broadcast rate of ⅜ pint/A, as called for in teh tests protocol. In the case of the HERBIMAX (Example 8), the broadcast rate was 1 quart/acre.

It can be seen from Table 1 that, although phytotoxicity of the herbicide compositions generally increased with the number of EO units in the silicone glycol under non-rain conditions, there was surprisingly found a maximum in plant injury after simulated rainfall when the silicone glycol contained 5, and particularly 4, EO units (i.e., Examples 5 and 4 of the present invention, respectively).

In a second experimental series, the procedure of Examples 1–7 were repeated, wherein silicone glycols having —OH end groups were mixed with BLAZER and the silicone glycol dispersant designated as DISPERSANT 1 (Table 2). Thus, these silicone glycols had the average structure

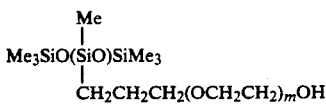

wherein m had the value indicated in the Table 2, below. In addition to the above silicone glycols, a commercial silicone glycol, SILWET L-77 (Union Carbide Corp., Danbury, CT), was included in Table 2 for comparison purposes (Examples 20–22). These herbicide formulations were evaluated according to the test protocol, described above. It should be noted that the Duncan statistics (i.e., superscripts) in Table 2, as well as those in Table 3, infra, relate to the second experimental series and are not to be compared to the statistics of the first series of Table 1.

DISPERSANT 1). Similarly, Examples 17–19 clearly demonstrate that the silicone glycol DISPERSANT 1 also results in poor rain fastness when used alone as the BLAZER adjuvant.

In the same (i.e., second) experimental series, various other dispersants were combined with silicone glycols having the average structure

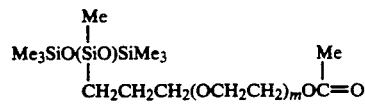

in which m had the value indicated in Table 3, below. These were formulated with BLAZER and tested according to the above described procedures (i.e., Test Protocol).

DISPERSANT 2 was a silicone glycol having the average formula

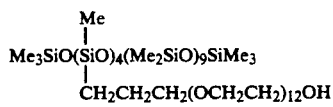

DISPERSANT 3 was an anionic surfactant, ammonium nonylphenoxypolyethoxysulfate (ALIPAL HF-433; GAF Corp., Wayne, NJ).

DISPERSANT 4 was a cationic surfactant, POLYQUART H (Henkel Corporation, Teaneck, NJ) which is described as a polyamine-polyglycol condensate.

TABLE 2

| Herbicide Dispersion | Ethylene Oxide Units (m) | Silicone Glycol Amount (gm) | DISPERSANT 1 Amount (gm) | Percent Injury to Plant | |
|---|---|---|---|---|---|
| | | | | No Rain | With Rain |
| Example 9 | 2 | 0.752 | 0.188 | 49[h,i] | 15[p,q] |
| Example 10 | 3 | 0.752 | 0.188 | 81[a,b,c] | 15[p,q] |
| Example 11 | 4 | 0.752 | 0.188 | 85[a,b] | 73[e,f] |
| Example 12 | 4 | 0.752 | — | 66[f,g] | 16[p,q] |
| Example 13 | 4 | 0.94 | — | 50[h] | 10[q,r] |
| Example 14 | 5 | 0.752 | 0.188 | 78[c,d,e] | 21[o,p] |
| Example 15 | 6* | 0.752 | 0.188 | 83[a,b,c] | 25[n,o] |
| Example 16 | 7 (avg.) | 0.752 | 0.188 | 83[a,b,c] | 33[l,m] |
| Example 17 | — | — | 0.94 | 40[j,k] | 5[r,s] |
| Example 18 | — | — | 0.752 | 38[j,k,l] | 5[r,s] |
| Example 19 | — | — | 0.188 | 15[p,q] | 0[s] |
| Example 20 | (L-77) | 0.752 | 0.188 | 88[a] | 43[i,j,k] |
| Example 21 | (L-77) | 0.94 | — | 80[b,c,d] | 44[h,i,j] |
| Example 22 | (L-77) | 0.752 | — | 81[a,b,c] | 36[k,l,m] |
| Control - (No BLAZER, No adjuvants) | | | | 0[s] | 0[s] |

*allyl-terminated glycols having 5 or fewer ethylene oxide units stripped off before preparation of the corresponding silicone glycol.

It is apparent that the herbicide formulation containing the silicone glycol having four ethylene oxide units (i.e., m=4), in combination with DISPERSANT 1, provided significantly improved phytotoxicity after exposure to simulated rain conditions. Additionally, it can be seen from Table 2 (compare Examples 11–13) that the silicone glycol having four ethylene oxide units does not impart improved rainfastness to the BLAZAR in the absence of the dispersant silicone glycol (i.e., DISPERSANT 5 was a nonionic surfactant, BRIJ 97 (ICI United States, Wilmington, DE) which is described as a polyoxyethylene(10) oleyl ether.

All of the above dispersants imparted water dispersibility to the silicone glycols, as evidenced by the formation of stable water dispersions in the above described Test Protocol 1 wherein 0.752 grams of the silicone glycol and 0.188 grams of the dispersant were used as previously outlined. However, as shown in Table 3, none of these combinations resulted in improved rain fastness.

TABLE 3

| Herbicide Dispersion | Ethylene Oxide Units | Dispersant Employed | Percent Injury to Plant | |
|---|---|---|---|---|
| | | | No Rain | With Rain |
| Example 23 | 2 | DISPERSANT 2 | 15[p,q] | 0[s] |
| Example 24 | 4 | DISPERSANT 2 | 20[o,p] | 5[r,s] |
| Example 25 | 6* | DISPERSANT 2 | 61[g] | 5[r,s] |
| Example 26 | 2 | DISPERSANT 3 | 10[q,r] | 0[s] |
| Example 27 | 4 | DISPERSANT 3 | 20[o,p] | 5[r,s] |
| Example 28 | 6* | DISPERSANT 3 | 73[c,f] | 30[m,n] |
| Example 29 | 2 | DISPERSANT 4 | 5[r,s] | 0[s] |
| Example 30 | 4 | DISPERSANT 4 | 15[p,q] | 0[s] |
| Example 31 | 6* | DISPERSANT 4 | 49[h,i] | 0[s] |
| Example 32 | 2 | DISPERSANT 5 | 20[o,p] | 0[s] |
| Example 33 | 4 | DISPERSANT 5 | 21[o,p] | 5[r,s] |
| Example 34 | 6* | DISPERSANT 5 | 50[h] | 25[n,o] |

*allyl-terminated glycols having 5 or fewer ethylene oxide units stripped off before preparation of the corresponding silicone glycol.

When the various dispersants in the above examples (i.e., DISPERSANT 2, 3, 4 and 5) were used as the sole adjuvant at a level of 0.188 grams, the percent injury (with rain) was zero in each case.

In a third experimental series (Examples 35–38), water dispersions of herbicide compositions were prepared according to the methods of Examples 1–7, wherein the silicone glycols had the average structure

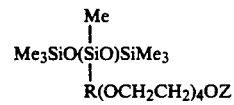

in which m had the values indicated in the Table 4, below. Four parts of each of these silicone glycols was blended with one part DISPERSANT 1. This blend was then mixed with BASAGRAN herbicide and applied to velvetleaf plants according to the above described test protocol (i.e., BASAGRAN substituted for BLAZER). In this experimental series, the water spray (simulated rainfall) was started two hours after application of the herbicidal compositions in order to evaluate rainfastness (as opposed to the 15 minutes utilized for BLAZER). The BASAGRAN was obtained from BASF Wyandotte Corp., Parsippany, NJ and is described as 3-isopropyl-1H-2,1,3-benzothiadiazin-4(3H)-one 2,2-dioxide (bentazon). In this series, the application rates were 0.28 lb/A for the BASAGRAN and 0.75 pint/A for the total silicone adjuvant blend (i.e., the above named silicone glycol and DISPERSANT 1). The value 0.28 lb/A was chosen as a rate yielding about 50% injury to the plant. Table 4 shows velvetleaf plant injury results for these adjuvant combinations, wherein the superscripts again signify Duncan statistics.

TABLE 4

| Herbicide Dispersion | Ethylene Oxide Units (m) | Purity of the Silicone Glycol by Gas Chromatography (%) | Percent Injury to Plant | |
|---|---|---|---|---|
| | | | No Rain | With Rain |
| Example 35 | 2 | 82 | 48[c,d] | 48[c,d] |
| Example 36 | 4 | 84 | 59[b] | 56[b] |
| Example 37 | 5 | 81 | 70[a] | 60[b] |
| Example 38 | 6* | >80 | 55[b,c] | 45[d] |
| Control - (No BASAGRAN, No adjuvants) | | | 0[f] | 0[f] |
| Control - (BASAGRAN Only) | | | 0[f] | 0[f] |

*allyl-terminated glycols having 5 or fewer ethylene oxide units stripped off before preparation of the corresponding silicone glycol.

It is apparent that the BASAGRAN herbicide formulations containing silicone glycols having four or five ethylene oxide units (i.e., m=4 or 5), in combination with DISPERSANT 1, provided significantly improved phytotoxicity after exposure to simulated rain conditions.

We claim:

1. A silicone glycol having the structure

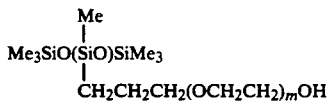

wherein Me denotes a methyl radical, R is a divalent alkylene group having 2 to 6 carbon atoms and Z is selected from the group consisting of hydrogen and an acetyl group.

2. The silicone glycol according to claim 1, wherein Z is hydrogen.

3. The silicone glycol according to claim 2, wherein R is a trimethylene group.

4. A silicone glycol having the structure

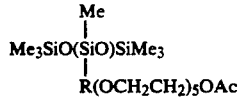

wherein Me denotes a methyl radical, R is a divalent alkylene group having 2 to 6 carbon atoms and Ac represents an acetyl group.

5. The silicone glycol according to claim 4, wherein R is a trimethylene group.

* * * * *